United States Patent
Lee et al.

(10) Patent No.: US 11,413,254 B2
(45) Date of Patent: Aug. 16, 2022

(54) APPLICATION FOR (2R, 4R)-1,2,4-TRIHYDROXYHEPTADEC-16-YNE IN PREPARATION OF PHARMACEUTICAL COMPOSITION FOR PREVENTING OR TREATING HEPATIC INJURY

(71) Applicant: KAOHSIUNG MEDICAL UNIVERSITY, Kaohsiung (TW)

(72) Inventors: Jin-Ching Lee, Kaohsiung (TW); Hsun-Shuo Chang, Kaohsiung (TW); Ih-Sheng Chen, Kaohsiung (TW); Chin-Kai Tseng, Taipei (TW); Chun-Kuang Lin, Kaohsiung (TW)

(73) Assignee: NORBEL BABY CO., LTD., Kaohsiung (TW)

(*) Notice: Subject to any disclaimer, the term of this patent is extended or adjusted under 35 U.S.C. 154(b) by 364 days.

(21) Appl. No.: 16/471,576

(22) PCT Filed: Dec. 22, 2016

(86) PCT No.: PCT/CN2016/111409
§ 371 (c)(1),
(2) Date: Jun. 20, 2019

(87) PCT Pub. No.: WO2018/112816
PCT Pub. Date: Jun. 28, 2018

(65) Prior Publication Data
US 2020/0230075 A1     Jul. 23, 2020

(51) Int. Cl.
    *A61K 31/047*     (2006.01)
    *A61P 1/16*     (2006.01)
    *A61K 9/00*     (2006.01)

(52) U.S. Cl.
CPC .............. *A61K 31/047* (2013.01); *A61P 1/16* (2018.01); *A61K 9/0019* (2013.01); *A61K 9/0053* (2013.01)

(58) Field of Classification Search
CPC .................................................... A61K 31/047
USPC ........................................................ 514/738
See application file for complete search history.

(56) References Cited

FOREIGN PATENT DOCUMENTS

TW     201636039 A     10/2016

OTHER PUBLICATIONS

Patel et a. "Hepatitis C and hepatic steatosis," Q.J. Med. 2010, vol. 103, pp. 293-303 (Year: 2010).*
Clinical Manifestations, Diagnosis and Treatment of Dengue Fever, Pulbished by the Taiwan Center for Disease Control, The Ministry of Health and Welfare, May 2015.

* cited by examiner

*Primary Examiner* — Shengjun Wang
(74) *Attorney, Agent, or Firm* — Hannah Tien (57) ABSTRACT

The present invention provides a use of (2R,4R)-1,2,4-trihydroxy heptadec-16-yne or a pharmaceutically acceptable salt, a tautomer, a stereoisomer or an enantiomer thereof in the preparation of a pharmaceutical composition for preventing or treating liver injury.

2 Claims, 7 Drawing Sheets

APPLICATION FOR (2R, 4R)-1,2,4-TRIHYDROXYHEPTADEC-16-YNE IN PREPARATION OF PHARMACEUTICAL COMPOSITION FOR PREVENTING OR TREATING HEPATIC INJURY

CROSS-REFERENCES TO RELATED APPLICATIONS

This patent application is a U.S. National Stage Application of PCT/CN2016/111409, filed Dec. 22, 2016, which is incorporated herein by reference in its entirety.

FIELD OF THE INVENTION

The present invention provides a use of (2R,4R)-1,2,4-trihydroxy heptadec-16-yne or a pharmaceutically acceptable salt, a tautomer, a stereoisomer or an enantiomer thereof in the preparation of a pharmaceutical composition for preventing or treating liver injury.

BACKGROUND OF THE INVENTION

Liver disease is prevalent in Taiwan, which includes alcoholic hepatitis, chemical hepatitis, drug-induced liver disease, fatty liver, viral hepatitis, hereditary liver diseases, etc., which induce liver injury caused by acute or chronic inflammation, eventually resulting in cirrhosis and even liver cancer after a period of time. Although currently there is no uniform definition of liver injury, any reasons that lead to abnormal liver function indicators indicates the presence of liver injury. Liver injury is followed by hepatocellular degeneration, liver necrosis, and fibrous tissue hyperplasia, leading to changes in normal liver tissues, which in turn induce a series of pathological changes and secondary diseases. Therefore, early diagnosis, care and treatment of liver injury is critical to prevent it from further development, thereby restoring liver function to normal. Currently, there are many choices of liver-protecting health foods available on the market, however, none of them has a significant effect at an affordable price.

DETAILED DESCRIPTION OF THE INVENTION

The present invention discloses an effect of a compound (2R,4R)-1,2,4-trihydroxy heptadec-16-yne on prevention or treatment of liver injury.

The present invention provides a use of (2R,4R)-1,2,4-trihydroxy heptadec-16-yne or a pharmaceutically acceptable salt, a tautomer, a stereoisomer or an enantiomer thereof in the preparation of a pharmaceutical composition for preventing or treating liver injury.

The liver injuries according to the present invention comprise acute and chronic liver injuries, which comprise (but are not limited to) the liver injuries caused by chemical hepatitis, alcoholic hepatitis, fatty acid liver disease, hepatitis virus or non-hepatitis virus infections, immune dysfunction, liver fibrosis, or liver cancer.

The chemical hepatitis according to the present invention, the inducing substances of which comprise (but are not limited to) halogen-containing organic compounds such as ethylene dichloride, carbon tetrachloride, propylene dichloride, carbon tetrabromide, 1,1,2,2-tetrachloroethane, acetylene tetrabromide, ethylene dibromide, etc.; naphthalene compounds such as various chlorinated naphthalenes, for example, trichloronaphthalene, tetrachloronaphthalene, pentachloronaphthalene, octachloronaphthalene, etc.; amide compounds such as dimethyl formamide, dimethyl acetamide, etc.; nitrosamine compounds such as N-nitrosodimethylamine, etc.; furan compounds such as tetrahydrofuran, etc.; aliphatic nitrogen-containing compounds such as 2-nitropropane, etc.; aromatic amine compounds such as 4,4'-diaminodiphenylmethane, etc.; aliphatic amine-containing compounds such as 2,4,6-trinitrotoluene, etc.; metal elements or compounds such as arsenic, beryllium, thallium, copper, selenium, etc., and other compounds, or chromic acid or chromate, etc.; agrochemicals such as insecticides, herbicides, or fumigants, for example, DDT, chlorine- or other halogen-containing organic compounds, bipyridine compounds such as paraquat, etc., nitrophenol or chlorophenol, and compounds used as agrochemicals; ethylene compounds such as vinyl chloride, vinylidene chloride, vinyl toluene, etc.; and others such as diphenyl, polychlorinated biphenyl (PCB), allyl alcohol, chlorine gas, phosphorus, ethylene oxide, etc.

A use of the pharmaceutical composition of the present invention is for the treatment of fatty acid liver diseases, wherein the fatty acid liver diseases comprise (but are not limited to) non-alcoholic fatty acid liver disease (NAFLD), nonalcoholic steatohepatitis (NASH), fatty liver disease caused by hepatitis, fatty liver disease caused by obesity, fatty liver disease caused by diabetes, fatty liver disease caused by insulin resistance, fatty liver disease caused by hypertriglyceridemia, abetalipoproteinemia, glycogen storage disease, Weber-Christian Syndrome, Wolman's disease, acute fatty liver of pregnancy and lipid malnutrition.

Aspartate aminotransferase (GOT/AST) and alanine aminotransferase (GPT/ALT) in serum are commonly used as indicators for detecting liver injury. In several embodiments of the present invention, (2R,4R)-1,2,4-trihydroxy heptadec-16-yne decreases the elevated liver function indicators induced by carbon tetrachloride, alcohol, or high-fat diet, wherein the liver function indicators comprise aspartate aminotransferase and alanine aminotransferase.

In one embodiment, (2R,4R)-1,2,4-trihydroxy heptadec-16-yne is administered to a subject suffering from liver injury induced by carbon tetrachloride. The results show that (2R,4R)-1,2,4-trihydroxy heptadec-16-yne is effective in the treatment of hepatocellular injury and tissue abnormalities caused by chemical hepatitis.

In one embodiment, (2R,4R)-1,2,4-trihydroxy heptadec-16-yne is administered to a subject suffering from liver injury induced by alcohol (ethanol). The results show that (2R,4R)-1,2,4-trihydroxy heptadec-16-yne is effective in the treatment of hepatocellular injury and tissue abnormalities caused by alcoholic hepatitis.

In one embodiment, (2R,4R)-1,2,4-trihydroxy heptadec-16-yne is administered to a subject suffering from liver injury induced by high-fat diet. The results show that (2R,4R)-1,2,4-trihydroxy heptadec-16-yne is effective in the treatment of hepatocellular injury and tissue abnormalities caused by fatty acid liver disease.

The composition of the present invention can be in the form of a solid, a solution, an emulsion, a dispersion, a micelle, a liposome, and other composition products containing one or more of the ingredients of the present invention as active ingredients, or mixed with an organic or inorganic carrier or excipient so as to be suitable for enteral or parenteral administration. The active ingredients can be mixed with, for example, a pharmaceutically acceptable, usually non-toxic carrier such as a tablet, a pill, a capsule, a suppository, a solution, an emulsion, a suspension, and any other suitable forms for use. The carriers which can be used comprise glucose, lactose, arabic gum, gelatin, mannitol, starch paste, magnesium trisilicate, talc, corn starch, keratin, colloidal silica, potato starch, urea, medium chain triglycerides, dextran, and other carriers suitable for formulation preparation, and other carriers in solid, semi-solid or liquid form. In addition, stabilizers, thickeners and colorants and flavoring agents can also be used.

The composition of the present invention can be administered orally, for example, as tablets, troches, lozenges, aqueous or oil suspensions, dispersible powders or granules, emulsions, hard or soft capsules, or syrups or elixirs. The composition for oral use can be prepared according to various known pharmaceutical composition preparation methods, and the composition can contain one or more sweeteners such as sucrose, lactose or saccharin, flavoring agents such as mint, wintergreen oil or cherry, colorants and preservatives to provide aesthetic appearance and mouthfeel for pharmaceuticals. Tablets mixed with active ingredients and pharmaceutically acceptable non-toxic excipients can also be prepared by known methods. The excipients which can be used are, for example, (1) inert diluents such as calcium carbonate, lactose, calcium phosphate, or sodium phosphate; (2) granulating agents and disintegrating agents such as corn starch, potato starch, or alginic acid; (3) binders such as tragacanth gum, corn starch, gelatin or arabic gum; and (4) lubricants such as magnesium stearate, stearic acid, or talc. The tablets can be uncoated or coated by known techniques to delay disintegration and absorption in the gastrointestinal tract, thereby providing a sustained action over a longer period of time. For example, time delay materials such as glyceryl monostearate or glyceryl distearate can be used, or techniques such as those described in the U.S. Pat. Nos. 4,256,108, 4,160,452, and 4,265,874 can be used for coating to produce osmotic therapeutic tablets to control the release of drug effects.

In some cases, the compositions for oral use can be in the form of hard gelatin capsules, wherein the active ingredients are mixed with inert solid diluents such as calcium carbonate, calcium phosphate or kaolin. They can also be in the form of soft gelatin capsules, wherein the active ingredients are mixed with water or oil media, such as peanut oil, liquid paraffin or olive oil.

An embodiment of the composition of the present invention can also be in the form of a sterile injectable suspension. The suspension can be formulated according to known methods with suitable dispersants or wetting agents and suspending agents. The sterile injectable formulation can also be a sterile injectable solution or a suspension dissolved in a non-toxic, parenterally acceptable diluent or solvent, for example as a solution in 1,3-butanediol. Sterile, non-volatile oils are commonly used as solvents or suspending media. For this purpose, any mild fixing oil can be used, including synthetic mono- or diglycerides, fatty acids (including oleic acid), naturally occurring plant oils such as sesame oil, coconut oil, peanut oil, cottonseed oil, etc., or synthetic fatty acid carriers such as ethyl oleate or the likes. Buffering agents, preservatives, antioxidants, etc. can be combined as needed.

One embodiment of the composition of the present invention can also be administered in the form of a suppository in the rectal cavity. The composition is prepared by mixing the drug with a suitable, non-irritating excipient, such as a synthetic glyceride of cocoa butter or polyethylene glycol. The composition is solid at room temperature but liquefied and/or dissolved in the rectal cavity to release the drug.

Since individual subjects may exhibit broad variations in the severity of the symptoms, and each drug has its own unique therapeutic characteristics, the subjects' responses to the treatment should be determined by physicians for the use of the composition of the present invention, and the dosage should be adjusted accordingly.

EXAMPLES

Unless otherwise specifically stated in the text, the singular form "a" and "the" as used in the specification and claims include the plural form of the mentioned. For example, "a derivative" includes a plurality of such derivatives, and "a subject" includes one or more subjects.

Further, unless otherwise stated, the use of "or" means "and/or." Similarly, "comprising" and "including" are used interchangeably and are not intended to be limiting.

It will be further understood that when the term "comprising" is used in describing each of the embodiments, it will be understood by those artisans skilled in the art that under specific circumstances, the language "consisting essentially of" or "consisting of" may be used to describe the embodiment.

Unless otherwise defined, all technical and scientific terms used herein have the same meaning as commonly understood by one of ordinary skill in the art to which this disclosure pertains. Although methods and materials similar or equivalent to those described herein can be used in the practice of the disclosed methods and compositions, only exemplary methods, devices, and substances are described herein.

The disclosures discussed above and throughout the article are provided solely for disclosures prior to the filing date of the instant application. Nothing herein is to be construed as an admission that the inventors of the present invention cannot claim priorities to these disclosures.

The present invention provides an use of (2R,4R)-1,2,4-trihydroxy heptadec-16-yne or a pharmaceutically acceptable salt, a tautomer, a stereoisomer or an enantiomer thereof in the preparation of a pharmaceutical composition for preventing or treating liver injury.

The preparation method of (2R,4R)-1,2,4-trihydroxy heptadec-16-yne in the instant disclosure can be referred to the Taiwan Invention Patent Publication No. TW201636039A. About 11.9 kg of immature avocado fruit was sliced, then dried in an oven at 50° C. to obtain a dried avocado sample. The weight was approximately 2.3 kg. The dried avocado sample was extracted with methanol at room temperature and the extraction step was repeated three times to obtain a methanol extract with higher purity. Ethyl acetate (EtOAc) solution (EtOAc: $H_2O$ was 1:1) was added to separate the methanol extract into an ethyl acetate-soluble fraction (EtOAc-soluble fraction) and a water-soluble fraction ($H_2O$-soluble fraction). Approximately 100 grains of the ethyl acetate-soluble fraction was added to a column filled with silica gel (70-230, Merck) for chromatography and purification. After being eluted with a concentration gradient elution of n-hexane-ethyl acetate (n-hexane-EtOAc), 12 fractions (A-1 to A-12) were obtained. Then, 10.5 g of the A-12 fraction was recrystallized with n-hexane to obtain crystals (A-12-C) and mother solution (A-12-M). Next, 10 g of A-12-M was analyzed by chromatography on a silica gel-filled column (230-400 mesh, Merck), and eluted with a concentration gradient elution of n-hexane-ethyl acetate to obtain 7 fractions (A-12-M-1 to A-12-M-7). Subsequently, 7.3 g of A-12-M-4 was analyzed by chromatography on a RP-C 18 column (spherical C 18 100 A reversed-phase silica gel (RP-18), 20-40 μM, Silicycle), and Eluted with acetone-water (1:1), analyzed and compared by nuclear magnetic resonance (NMR), to obtain approximately 113 mg of (2R,4R)-1,2,4-trihydroxy heptadec-16-yne, as shown in formula (I).

For the convenience of explanation, in the following description (2R,4R)-1,2,4-trihydroxy heptadec-16-yne is abbreviated as TY.

The following examples are not intended to be limiting, but merely to present a variety of aspects of the present invention.

Figure 1:
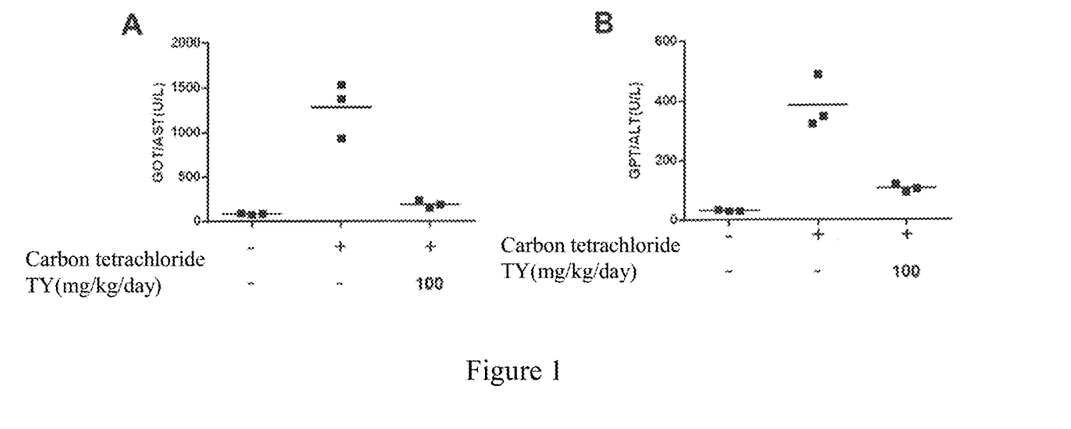
FIG. 1: TY decreases abnormal liver function indicators resulted from carbon tetrachloride. Serum (A) GOT/AST and (B) GPT/ALT of the rats with acute hepatitis resulted from carbon tetrachloride are tested. Three male Wistar rats are included in each group of experiments.

Example 1. The effect of TY for the treatment of acute hepatitis caused by carbon tetrachloride was tested. Nine male Wistar rats (200-250 g) were randomly divided into 3 groups, 3 Wistar rats in each group, they were: 1. Healthy control group: force fed with drug solvent and intraperitoneal injection of olive oil (2.5 mg/kg) of the same volume as TY; 2. Negative control group (carbon tetrachloride and physiological saline): force fed with physiological saline and intraperitoneal injection of 20% carbon tetrachloride/olive oil of the same volume as TY; 3. Experimental group (carbon tetrachloride and 100 mg/kg/day of TY): force fed 100 mg/kg/day of TY and intraperitoneal injection of 20% carbon tetrachloride/olive oil. First, the drug solvent or TY was administered by force feeding once daily and the first force feeding was defined as the first day. One hour after force feeding on the fourth day, Group 1 was given intraperitoneal injection of olive oil (2.5 mg/kg), Groups 2-3 were given intraperitoneal injection of 20% carbon tetrachloride/olive oil (2.5 mg/kg), fasted 12 hours after injection, all Wistar rats were sacrificed 12 hours after fasting. Prior to being sacrificed, blood was collected from the heart and serum was separated for analysis of the biochemical function of the liver. FIGS. 1A and 1B showed that carbon tetrachloride significantly increased the liver function indicators GOT/AST and GPT/ALT of the Wistar rats, while TY significantly decreased the liver function indicators GOT/AST and GPI/ALT increased by carbon tetrachloride. This result showed that TY was capable of treating abnormal liver function caused by carbon tetrachloride.

Figure 2:
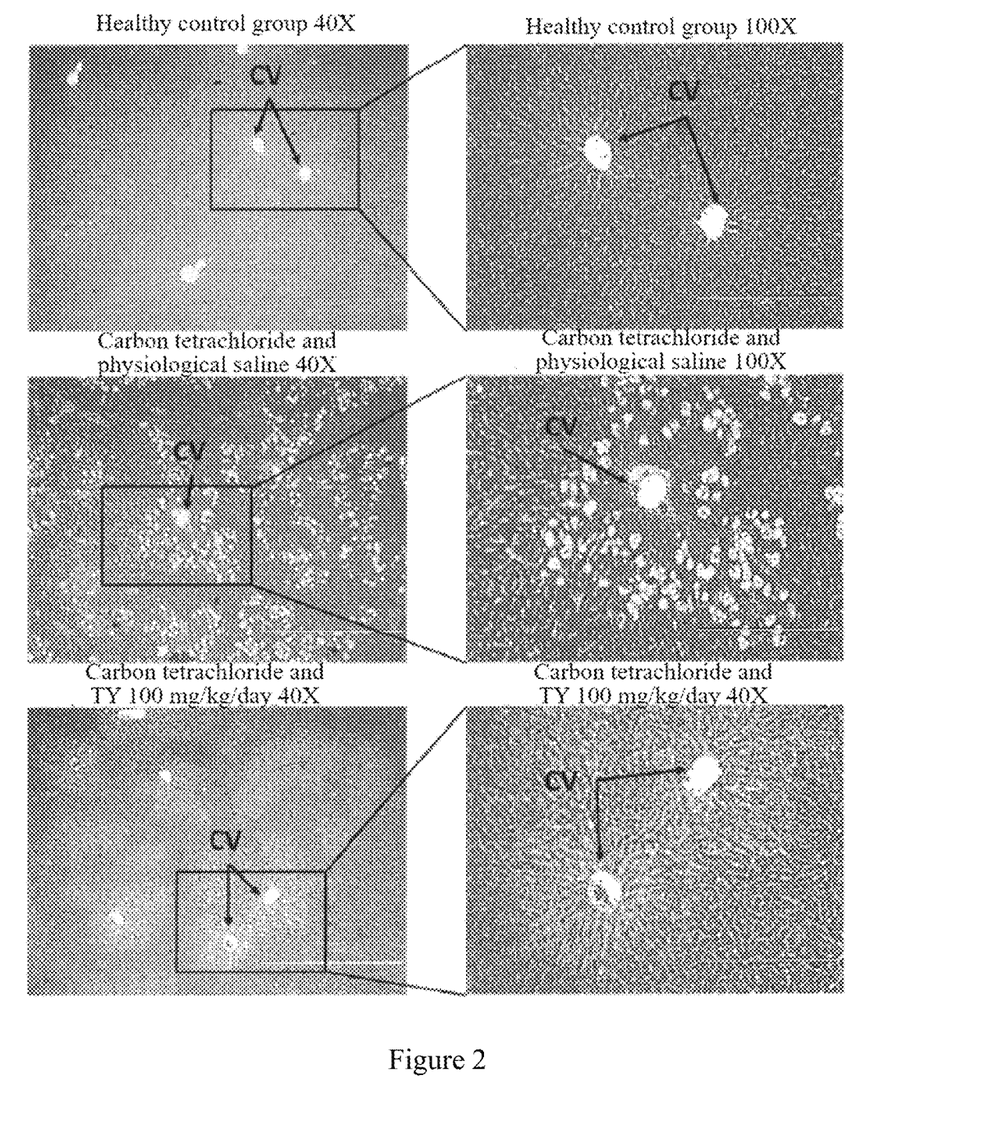
FIG. 2: TY reduces hepatocellular necrosis caused by carbon tetrachloride. The histological patterns of liver cells of the rats with acute hepatitis caused by carbon tetrachloride are observed by H&E staining. Three male Wistar rats are included in each group of experiments.

Example 2. Hepatocellular injury and necrosis caused by carbon tetrachloride were treated by TY. Nine male Wistar rats (200-250 g) were randomly divided into 3 groups, 3 Wistar rats in each group, they were: 1. Healthy control group: force fed with drug solvent of the same volume as TY and intraperitoneal injection of olive oil (2.5 mg/kg); 2. Negative control group (carbon tetrachloride and physiological saline): force fed with physiological saline and intraperitoneal injection of 20% carbon tetrachloride/olive oil of the same volume as TY; 3. Experimental group (carbon tetrachloride and 100 mg/kg/day of TY): force fed 100 mg/kg/day of TY and intraperitoneal injection of 20% carbon tetrachloride/olive oil. First, the physiological saline or TY was administered by force feeding once daily, and the first force feeding was defined as the first day. One hour after the force feeding on the fourth day, Group 1 was given intraperitoneal injection of olive oil (2.5 mg/kg), Groups 2-3 were given intraperitoneal injection of 20% carbon tetrachloride/olive oil (2.5 mg/kg), respectively. The rats were fasted 12 hours after injection, all Wistar rats were sacrificed 12 hours after fasting. After the rats were sacrificed, livers were collected and soaked in formalin, and stained with H&E staining, then observed and images were taken with a microscope. FIG. 2 shows that significant liver injury was caused by injection of carbon tetracholoride (as compared to the Healthy control group), H&E staining indicated hepatocellular necrosis near the central vein and overall tissue structural disorganization, while TY was capable of effectively reducing hepatocellular necrosis near the central vein caused by carbon tetrachloride.

Figure 3:
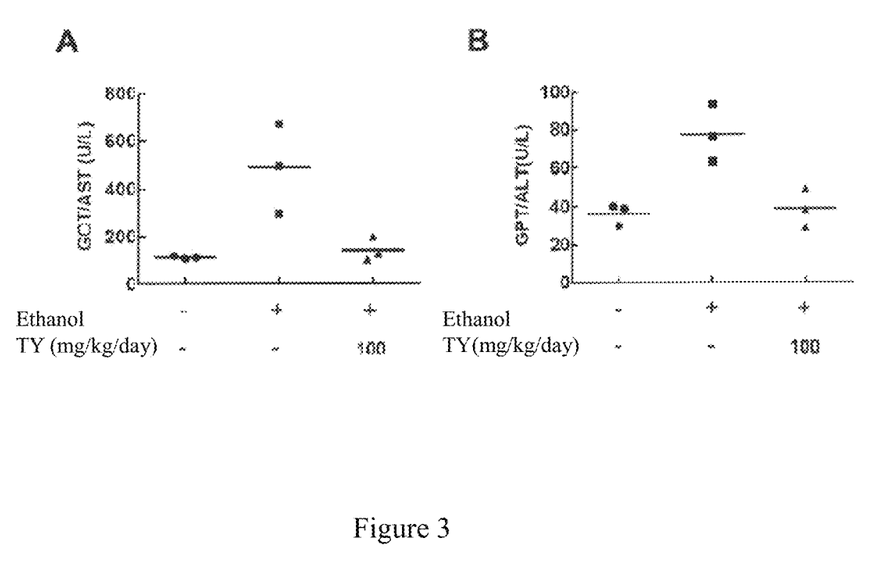
FIG. 3: TY decreases abnormal liver function indicators resulted from ethanol. Serum (A) GOT/AST and (B) GPT/ALT of the rats with acute hepatitis resulted from ethanol are observed. Three male Wistar rats are included in each group of experiments.

Example 3. The effect of TY on the treatment of acute hepatitis caused by alcohol (ethanol). Nine male Wistar rats (200-250 g) were randomly divided into 3 groups, 3 Wistar rats in each group, they were: 1. Healthy control group: force fed with physiological saline (2.5 mg/kg) of the same volume as TY; 2. Negative control group (ethanol and physiological saline): force fed with physiological saline of the same volume as TY and force fed with 50% ethanol; 3. Experimental group (ethanol and 100 mg/kg/day of TY): force fed 100 mg/kg/day of TY and force fed with 50% ethanol. First, the drug solvent or TY was administered by force feeding once daily, and the first force feeding was defined as the first day. One hour after force feeding on the fourth day, Group 1 was given physiological saline (2.5 mg/kg), Groups 2-3 were given intraperitoneal injection of 50% ethanol (2.5 mg/kg), respectively. The rats were force fed with ethanol again 12 hours after the first force feeding, and fasted 12 hours after the second force feeding. After being fasted for 12 hours, all Wistar rats were sacrificed. Prior to being sacrificed, blood was collected from the heart and serum was separated for analysis of the biochemical function of the liver. FIGS. 3A and 3B showed that ethanol significantly increased the liver function indicators GOT/AST and GPT/ALT of the Wistar rats, while TY significantly decreased the liver function indicators GOT/AST and GPI/ALT increased by ethanol. This result showed that TY was capable of treating abnormal liver function caused by ethanol.

Figure 4:
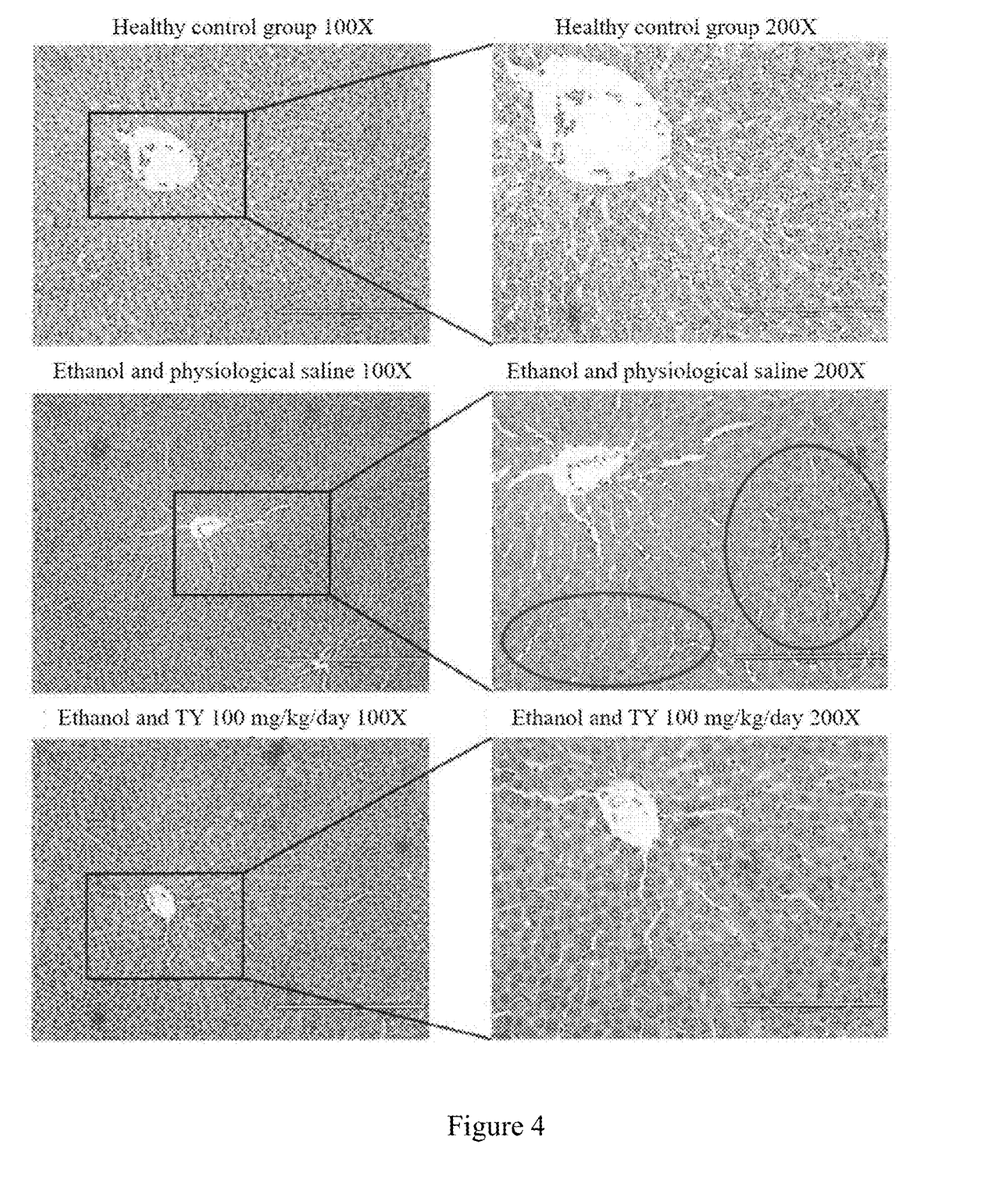
FIG. 4: TY reduces hepatocellular injury and abnormalities caused by ethanol. The histological patterns of liver cells of the rats with acute hepatitis caused by ethanol are observed by H&E staining. Three male Wistar rats are included in each group of experiments.

Example 4. Hepatocellular injury and abnormalities caused by alcohol (ethanol) were treated by TY. Nine male Wistar rats (200-250 g) were randomly divided into 3 groups, 3 Wistar rats in each group, they were: 1. Healthy control group: force fed with drug solvent of the same volume as TY and force fed with physiological saline (2.5 mg/kg); 2. Negative control group (ethanol and physiological saline): force fed with physiological saline of the same volume as TY and force fed with 50% ethanol; 3. Experimental group (Ethanol and 100 mg/kg/day of TY): force fed 100 mg/kg/day of TY and force fed with 50% ethanol. First, food solvent or TY was administered by force feeding once daily, and the first force feeding was defined as the first day. One hour after force feeding on the fourth day, Group 1 was given physiological saline (2.5 mg/kg), Groups 2-3 were given 50% ethanol injection (2.5 mg/kg), respectively. The rats were force fed with ethanol again 12 hours after the first force feeding, and fasted 12 hours after the second force feeding. After being fasted for 12 hours, all Wistar rats were sacrificed. After the rats were sacrificed, livers were collected and soaked in formalin, and stained with H&E staining, then observed and images taken with a microscope. FIG. 4 showed that significant liver injury and tissue abnormalities of the rats were caused by force feeding of ethanol (as compared to the Healthy control group, white illuminating spots in blue circles), H&E staining showed hepatocellular injury and overall tissue structural disorganization, while TY was capable of reducing the liver injury and tissue abnormalities caused by ethanol.

Figure 5:
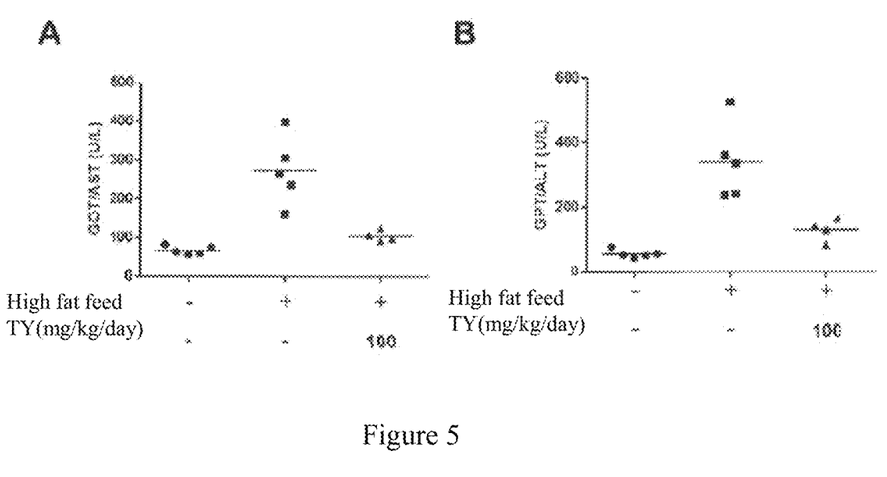
FIG. 5: TY reduces liver dysfunction caused by fatty acid liver disease induced by high fat feed. Serum (A) GOT/AST and (B) GPT/ALT of the mice with chronic hepatitis caused by high fat feed are tested. 4-5 male B6 mice are included in each group of experiments.

Example 5. Chronic hepatitis of fatty acid liver disease caused by high fat feed was treated by TY. 15 male, 8-10 weeks old of C57BL/6 (B6) mice (20-22 g) were randomly divided into 3 groups, 4-5 B6 mice in each group, they were: 1. Healthy control group: fed with normal feed (the percentage of fat calories 5-6%); 2. Negative control group: fed with high fat feed (the percentage of fat calorie 60%) and physiological saline; 3. Experimental group: animals were given the same high fat feed as the Negative control group and force fed with 100 mg/kg/day of TY. 1 week before liver injury was induced by high fat feed, the experimental samples began to be given daily, respectively, drug solvent of the same volume as TY to Groups 1 and 2, and 100 mg/kg/daily of TY to Group 3. After 1 week, Groups 2 and 3 began to be given high fat feed, and continuously to be force fed with the drug solvent of the volume same as TY and 100 mg/kg/day of TY for 18 weeks. The mice began to fast on the 18th week, and 12 hours after fasting, all B6 mice were sacrificed. Prior to being sacrificed, blood was collected from the heart and serum was separated for analysis of the biochemical function of the liver. FIGS. 5A and 5B showed that the high-fat feed significantly increased liver function indicators GOT/AST and GPT/ALT in B6 mice, while TY significantly decreased the liver function indicators GOT/AST and GPT/ALT increased by the high-fat feed. This result showed that TY was capable of treating liver function abnormalities of fatty acid liver disease induced by the high fat feed.

Figure 6:
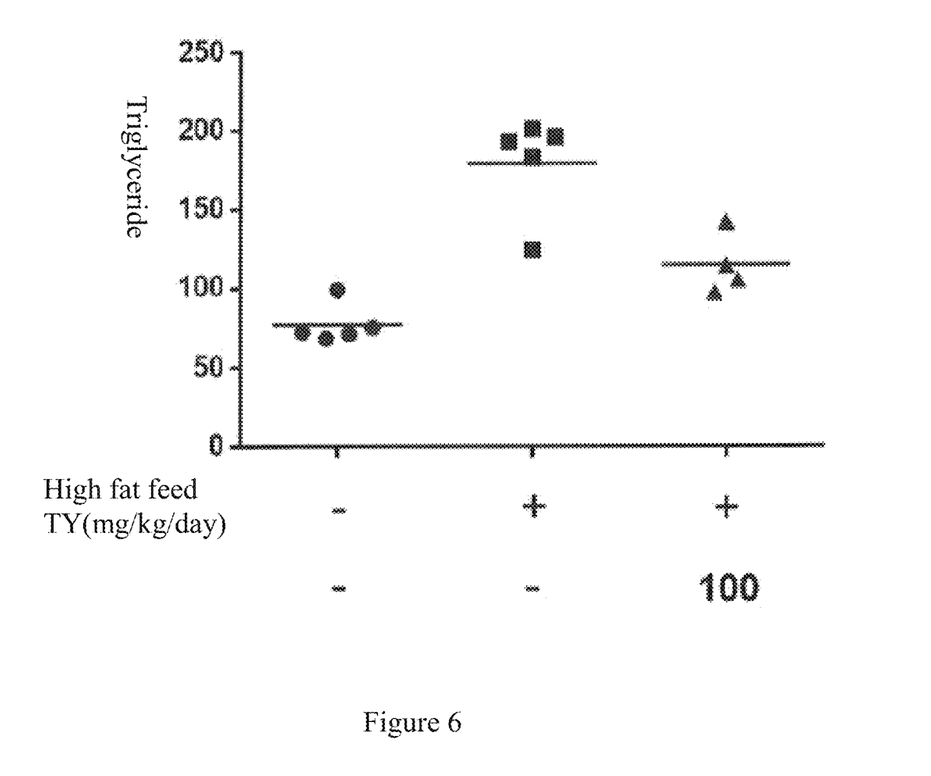
FIG. 6: TY decreases the triglyceride level in the serum of the mice with fatty acid liver disease induced by high fat feed. The triglyceride levels in the serum of the mice with chronic hepatitis caused by high fat diet are tested. 4-5 male B6 mice are included in each group of experiments.

Example 6. TY decreased serum triglyceride level of the mice with fatty acid liver disease induced by high fat feed. 15 male, 8-10 weeks old of C57BL/6 (B6) mice (20-22 g) were randomly divided into 3 groups, 4-5 B6 mice in each group, and they were: 1. Healthy control group: fed with normal feed (the percentage of fat calories 5-6%); 2. Negative control group: fed with high fat feed (the percentage of fat calorie 60%) and force fed with physiological saline (high fat feed and physiological saline); 3. Experimental group: animals were given the same high fat feed as the Negative control group and force fed with 100 mg/kg/day of TY (high fat feed and TY). 1 week before liver injury was induced by the high fat feed, the experimental samples began to be given daily, respectively, drug solvent of the same volume as TY to Groups 1 and 2, and 100 mg/kg of TY daily to Group 3. after 1 week, Groups 2 and 3 began to be given high fat feed, and continuously to be force fed with the drug solvent of the same volume as TY and 100 mg/kg/day of TY for 18 weeks. The mice began to fast on the 18th week, and 12 hours after fasting, all B6 mice were sacrificed. Prior to being sacrificed, blood was collected from the heart and serum was separated for analysis of the serum triglyceride level. FIG. 6 showed that the high-fat diet significantly increased the serum triglyceride level of the B6 mice, while TY significantly decreased the serum triglyceride level increased by the high-fat diet. This result showed that TY was capable of decreasing serum triglyceride level of the mice with fatty acid disease induced by the high fat feed.

Figure 7:
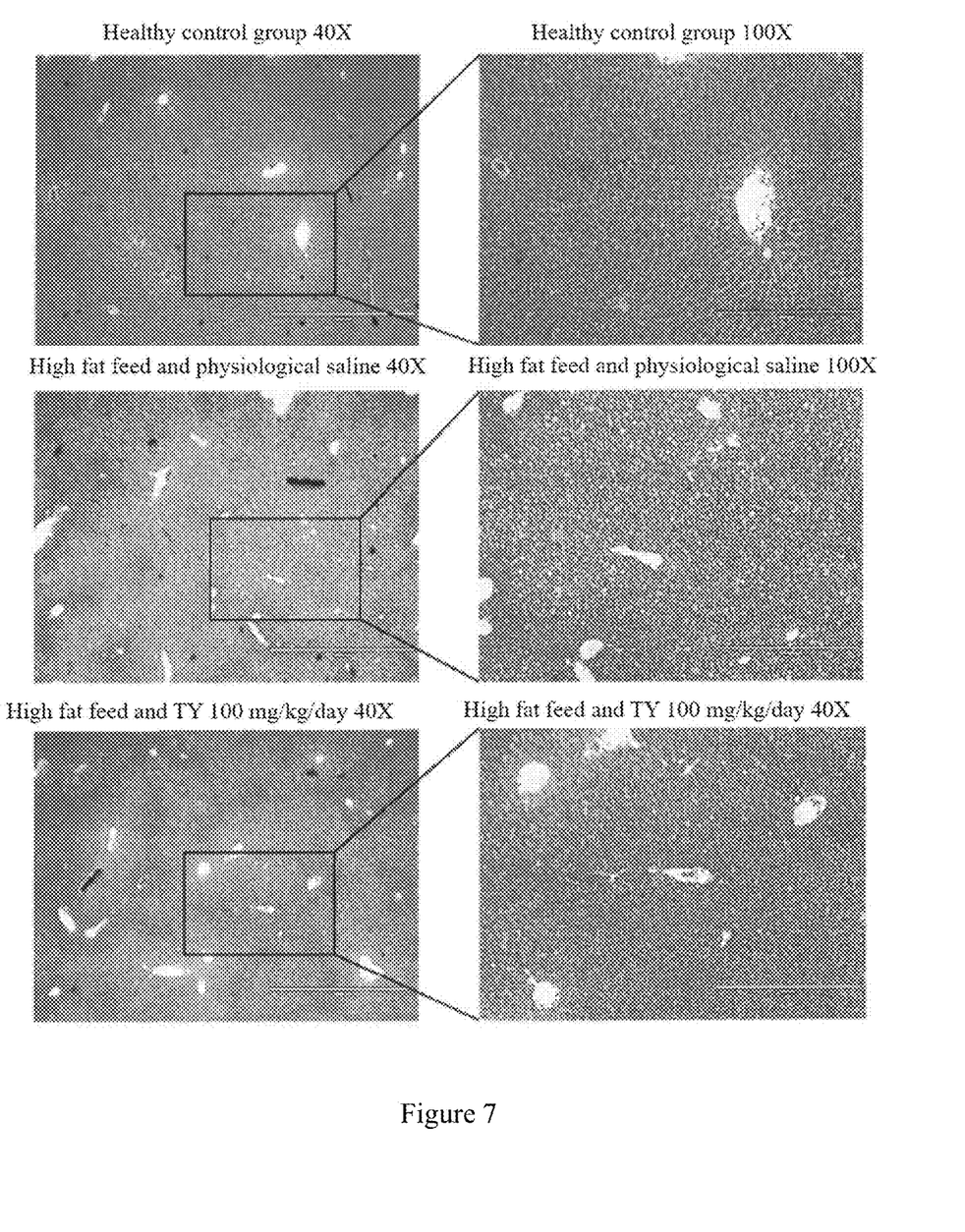
FIG. 7: Hepatocellular injury and abnormalities of fatty acid liver disease induced by high fat feed are treated by TY. The histological patterns of liver cells of the mice with chronic hepatitis caused by high fat feed are observed with H&E staining. 4-5 male B6 mice are included in each group of experiments.

Example 7. Hepatocellular injury and abnormalities of fatty acid disease induced by high fat feed were treated with TY. 15 male, 8-10 weeks old of C57BL/6 (B6) mice (20-22 g) were randomly divided into 3 groups, and 4-5 B6 mice in each group, they were: 1. Healthy control group: fed with normal feed (the percentage of fat calories 5-6%); 2. Negative control group: fed with high fat feed (the percentage of fat calorie 60%) and force fed with physiological saline; 3. Experimental group: animals were given the same high fat feed as the Negative control group and force fed with 100 mg/kg/day of TY (high fat feed and TY). 1 week before liver injury was induced by the high fat feed, the experimental samples began to be given daily, respectively, the drug solvent of the same volume as TY to Groups 1 and 2, and 100 mg/kg of TY daily to Group 3. After 1 week, Groups 2 and 3 began to be given high fat feed, and continuously to be force fed with the drug solvent of the same volume as TY and 100 mg/kg/day of TY for 18 weeks. The mice began to fast on the 18th week, and 12 hours after fasting, all B6 mice were sacrificed. After the mice were sacrificed, livers were collected and soaked in formalin, stained with H&E staining, and then observed and images taken with a microscope. FIG. 7 showed that significant liver injury and tissue abnormalities of the mice were caused by feeding the high fat feed (as compared to the Healthy control group). H&E staining showed hepatocellular injury and overall tissue structural disorganization (many empty bubbles were formed), but TY was capable of reducing the liver injury and tissue abnormalities caused by the high fat feed.

In order to enable one of ordinary skill in the art to which the present invention pertains to understand the method for manufacturing and using the technique, the present invention has been described and illustrated in sufficient detail, and various modifications, substitutions, or improvements should be encompassed within the spirit and scope of the present invention.

One skilled in the art readily appreciates that the present invention is well adapted to carry out the objects and obtain the ends and advantages mentioned, as well as those inherent therein. The animals, materials and processes and methods for producing them are representative of the most preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method of treating a liver injury, comprising administering a pharmaceutical composition comprising a therapeutically effective amount of (2R,4R)-1,2,4-trihydroxy heptadec-16-yne or a pharmaceutically acceptable salt, a tautomer, a stereoisomer or an enantiomer thereof to a subject suffering from the liver injury caused by chemical hepatitis, alcoholic hepatitis, or fatty acid liver disease, wherein the fatty acid liver disease is not induced by virus.

2. The method of claim 1, wherein the administration route of the pharmaceutical composition is one or a combination selected from the following group: a tablet, a lozenge, an aqueous or oil suspension, dispersible powders or granules, an emulsion, a hard or soft capsule, a syrup or elixir, or an injection.

* * * * *